(12) United States Patent
Runglertkriangkrai

(10) Patent No.: US 7,918,901 B2
(45) Date of Patent: Apr. 5, 2011

(54) HAIR CONDITIONING COMPOSITION COMPRISING AMINE-TYPE CATIONIC SURFACTANT AND DIRECT DYE

(75) Inventor: Siriporn Runglertkriangkrai, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/139,184

(22) Filed: Jun. 13, 2008

(65) Prior Publication Data

US 2008/0311068 A1 Dec. 18, 2008

Related U.S. Application Data

(60) Provisional application No. 60/934,637, filed on Jun. 15, 2007.

(51) Int. Cl.
*A61Q 5/10* (2006.01)
*A61Q 5/12* (2006.01)

(52) U.S. Cl. ............. 8/405; 8/426; 8/435; 8/552; 8/581; 8/637.1; 424/70.27

(58) Field of Classification Search ............... 8/405, 426, 8/435, 552, 581, 637.1; 424/70.27
See application file for complete search history.

(56) References Cited

U.S. PATENT DOCUMENTS

| 4,678,475 A | 7/1987 | Hoshowski |
| 4,964,874 A | 10/1990 | Saphakkul |
| 6,468,515 B1 * | 10/2002 | Uchiyama et al. ......... 424/70.27 |
| 2004/0096412 A1 | 5/2004 | Uehara |
| 2004/0158939 A1 | 8/2004 | Wells |
| 2004/0158941 A1 * | 8/2004 | Geary et al. ...................... 8/406 |
| 2006/0078529 A1 | 4/2006 | Uchida |
| 2006/0096041 A1 | 5/2006 | Molenda |

FOREIGN PATENT DOCUMENTS

| EP | 1502578 A1 | 2/2005 |
| EP | 1714677 A1 | 10/2006 |
| EP | 1679061 B1 | 6/2007 |
| JP | 5043438 A2 | 2/1993 |
| JP | 5194161 A2 | 8/1993 |
| JP | 6271434 A2 | 9/1994 |
| JP | 2000128750 A2 | 5/2000 |
| JP | 2004059565 A2 | 2/2004 |
| JP | 2004107247 A2 | 4/2004 |
| WO | WO 0040213 A1 | 7/2000 |

OTHER PUBLICATIONS

STIC Search Report dated Apr. 30, 2009.*

* cited by examiner

*Primary Examiner* — Eisa B Elhilo
(74) *Attorney, Agent, or Firm* — Linda M. Sivik

(57) ABSTRACT

Disclosed is a hair conditioning composition comprising by weight: (a) from about 0.2% to about 10% of a cationic surfactant which is a salt of: (i) primary, secondary, and tertiary amines wherein the amines have one long alkyl or alkenyl group of from about 20 to about 24 carbon atoms; and (ii) acids such as 1-glutamic acid and lactic acid; (b) from about 1% to about 15% of a high melting point fatty compound; (c) from about 0.00005% to about 0.5% of a direct dye; and (d) an aqueous carrier. The composition of the present invention provide coloring benefits especially color enhancing and/or preventing color fade of colored hair, while providing improved conditioning benefits.

11 Claims, No Drawings

HAIR CONDITIONING COMPOSITION COMPRISING AMINE-TYPE CATIONIC SURFACTANT AND DIRECT DYE

CROSS REFERENCE TO RELATED APPLICATION

This application claims the benefit of U.S. Provisional Application No. 60/934,637, filed Jun. 15, 2007.

FIELD OF THE INVENTION

The present invention relates to a hair conditioning composition comprising: (a) a cationic surfactant which is a salt of: (i) primary, secondary, and tertiary amines wherein the amines have one long alkyl or alkenyl group of from about 20 to about 24 carbon atoms; and (ii) acids such as 1-glutamic acid and lactic acid; (b) a high melting point fatty compound; (c) a direct dye; and (d) an aqueous carrier. The composition of the present invention provides coloring benefits especially color enhancing of colored hair and/or preventing color fade of colored hair, while providing improved conditioning benefits.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds, are believed to provide a gel matrix which is suitable for providing a variety of conditioning benefits such as slippery feel during the application to wet hair and softness and moisturized feel on dry hair.

There is a need for hair conditioning compositions which provide coloring benefits while providing conditioning benefits. Such coloring benefit is, for example, at least one of the followings: coloring to non-colored hair, color enhancing of colored hair, preventing color fade of colored hair and grey blending.

European Patent Application Publication No. 1502578 discloses a transparent hair coloring conditioning agent comprising polyquaternium-37 and at least one direct acting cationic hair dye, and free from fatty alcohols, the agent being said to be especially suitable for rinse off application as well as leave in application. European Patent Application Publication No. 1502578 also discloses, in Example 4, the agent further comprising stearamidopropylamine.

However, it has been found that it is still not easy to obtain hair conditioning compositions which provide coloring benefits especially color enhancing of colored hair and/or preventing color fade of colored hair, while providing improved conditioning benefits.

Based on the foregoing, there remains a need for hair conditioning compositions which provide coloring benefits while providing improved conditioning benefits.

None of the existing art provides all of the advantages and benefits of the present invention.

SUMMARY OF THE INVENTION

The present invention is directed to a hair conditioning composition comprising by weight:

(a) from about 0.2% to about 10% of a cationic surfactant which is a salt of: (i) primary, secondary, and tertiary amines wherein the amines have one long alkyl or alkenyl group of from about 20 to about 24 carbon atoms; and (ii) acids selected from the group consisting of 1-glutamic acid, lactic acid, hydrochloric acid, malic acid, succinic acid, acetic acid, fumaric acid, tartaric acid, and mixtures thereof;
(b) from about 1% to about 15% of a high melting point fatty compound;
(c) from about 0.00005% to about 0.5% of a direct dye; and
(d) an aqueous carrier.

The conditioning compositions of the present invention provide coloring benefits especially color enhancing of colored hair and/or preventing color fade of colored hair, while providing improved conditioning benefits.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

It is believed that; by the use of amine-type cationic surfactant with C20-24, together with other required components, the composition of the present invention can provide coloring benefits especially color enhancing of colored hair and/or preventing color fade of colored hair, while providing improved conditioning benefits.

Preferably, the composition of the present invention is substantially free of anionic surfactants and anionic polymers, in view of compatibility with cationic surfactants, and stability of the gel matrix when formed by cationic surfactants and high melting point fatty compounds. In the present invention, "substantially free of anionic surfactants and anionic polymers" means that the composition contains 1% or less, preferably 0.5% or less, more preferably totally 0% of total of anionic surfactants and anionic polymers.

Cationic Surfactant

The composition of the present invention comprises a cationic surfactant. The cationic surfactant is included in the composition at a level by weight of from about 0.2% to about 10%, preferably from about 0.3% to about 8%, more preferably from about 0.4% to about 5%, in view of providing improved conditioning benefits together with high melting point fatty compounds.

The cationic surfactants of the present invention are salts of: (i) primary, secondary, and tertiary amines wherein the amines have one long alkyl or alkenyl group of from about 20 to about 24 carbon atoms; and (ii) acids selected from the group consisting of 1-glutamic acid, lactic acid, hydrochloric acid, malic acid, succinic acid, acetic acid, fumaric acid, tartaric acid, and mixtures thereof. The amines and acids are included in the compositions at a level such that the mole ratio of the amines to the acids is preferably from about 1:0.3 to about 1:2, more preferably from about 1:0.3 to about 1:1.3, still more preferably from about 1:0.4 to about 1:1.

The primary, secondary, and tertiary amines useful herein are, for example, those having the following formula:

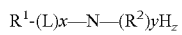

wherein $R^1$ is a straight or branched alkyl or alkenyl group of from about 20 to about 24 carbon atoms, preferably a straight alkyl group; L is a linkage selected from amido, amidoalkyl, amidopolyoxyalkyl, polyoxyalkyl, and mixtures thereof, wherein the alkyl has from 1 to 4 carbon atoms, preferably selected from amido or amidoalkyl in which the alkyl has from 1 to 4 carbon atoms; x is an integer of 0 or 1, preferably 1; $R^2$ is a $C_1$ to $C_4$ alkyl, alkenyl, alkoxyl, hydroxyalkyl, or polyoxyalkylene; y is an integer of from 0 to 2, preferably 2; z is an integer of form 0 to 2, preferably 0; y+z is an integer of 2.

Highly preferred amine is a tertiary amidoamine having the following general formula:

wherein $R^1$ is a straight or branched alkyl or alkenyl group of from about 20 to about 24 carbon atoms, preferably a straight alkyl group; m is an integer from 1 to 4; and $R^2$ is a $C_1$ to $C_4$ alkyl, alkenyl, alkoxyl, hydroxyalkyl, or polyoxyalkylene, preferably alkyl.

Such tertiary amidoamine useful herein include, for example: behenamidopropyldimethylamine, behenamidopropyldiethylamine, behenamidoethyldiethylamine, behenamidoethyldimethylamine, behenamidobutyldimethylamine, behenamidobutyldiethylamine, arachidamidopropyldimethylamine, arachidamidopropyldiethylamine, arachidamidoethyldiethylamine, arachidamidoethyldimethylamine, arachidamidobutyldimethylamine, and arachidabutyldiethylamine.

It has been surprisingly found that; the amine type cationic surfactant with C20-24 of the present invention provides improved deposition of direct dyes and also improved prevention of hair color loss, compared to other cationic surfactants. It is believed that, the amine type cationic surfactant with C20-24 of the present invention can provide such benefit because of its lower surface energy than those of such other cationic surfactants. Such other cationic surfactants include, for example, amine type cationic surfactants with shorter hydrocarbon chain such as stearamidopropyldimethylamine, and monoalkyl quaternized ammonium salts such as behenyl trimethyl ammonium salt.

High Melting Point Fatty Compound

The composition of the present invention comprises a high melting point fatty compound. The high melting point fatty compound is included in the composition at a level of from about 1% to about 15%, preferably from about 3% to about 10%, more preferably from about 5% to about 8% by weight of the composition, in view of providing improved conditioning benefits such as slippery feel during the application to wet hair, softness and moisturized feel on dry hair.

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Direct Dye

The composition of the present invention comprises a direct dye. The direct dye is included in the composition at a level of from about 0.00005% to about 15.0%, preferably from about 0.0001% to about 10.0%, more preferably from about 0.001% to about 5.0% by weight of the composition, in view of providing color enhancing benefit without changing original hair color tone, and minimizing the staining during application.

The direct dyes are those which are also called as non-oxidative dyes. The direct dyes useful herein include, for example: nonionic dyes such as nitro dyes, azo dyes, and anthraquinone dyes; cationic dyes such as basic dyes; and anionic dyes such as acidic dyes. It is known that some azo dyes and anthraquinone dyes can be classified as cationic dyes or anionic dyes, when they have cationic or anionic substitutions. The dye can be used alone or in combination with other dyes, according to target color of hair to which the composition is applied.

Preferably, the direct dyes useful herein are nonionic direct dyes, cationic direct dyes, and mixtures thereof, in view of compatibility with cationic surfactants. More preferably, the direct dyes useful herein are mixtures of nonionic direct dyes and cationic direct dyes. Still more preferably, the direct dyes useful herein are mixture of nitro dyes and basic dyes.

It is believed that; cationic dyes, especially basic dyes can deposit on the surface of hair by forming an ionic bonding with negatively charged hair surface, thus, can not be easily washed out from the hair. However, it is thought that; such cationic dyes tend to deposit unevenly on hair, and tend to deposit more on damaged portions such as hair tips rather than less damaged portions such as hair root.

It is believed that; nonionic dyes, especially nitro dyes can penetrate into hair evenly due to its neutral charge and smaller particle size, thus, can provide evenness on hair color. It is also believed that; nonionic dyes, especially nitro dyes can provide color enhancing and/or preventing color fade of colored hair while not changing the original color tone of the colored hair. However, it is thought that; such nonionic dyes tend to be easily washed off from the hair.

Thus, it is believed that; the combination of nonionic dyes and cationic dyes, especially the combination of nonionic nitro dyes and cationic basic dyes can provide evenness on hair color, and prolonged color enhancing and/or preventing color fade of colored hair.

Nonionic nitro dyes useful herein include, for example, 1,4-bis-[(2-hydroxyethyl)amino]-2-nitrobenzene, 1-(2-hydroxyethyl)amino-2-nitro-4-[di-(2-hydroxyethyl)amino] benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl) amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene (HC Violet No. 2), 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino] benzoic acid, 2-chloro-6-ethylamino-4-nitrophenol, 2-amino-6-chloro-4-nitrophenol, 4-[(3-hydroxypropyl) amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1, 4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoro-methylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), and 2,4-dinitro-1-hydroxynaphthalene Other nonionic direct dyes useful herein include, for example, 1,4-di-[(2,3-dihydroxypropyl)amino]-9,10-anthraquinone, 1,4-di-[(2-hydroxyethyl)amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl) amino]-9,10-anthraquinone (HC Red No. 8), 1,4-diamino-9, 10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di-(2-hydroxyethyl)amino)phenyl)amino)-5-((2-hydroxyethyl) amino)-2,5-cyclohexadien-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis-(dicyanomethylidene)indane, 1-[di-(2-hydroxyethyl)amino]-3-methyl-4-[(4-nitrophenyl)azo]benzene (CI11210, Disperse Red No. 17), 1-[di-(2-hydroxyethyl)amino]-4-[(4-nitrophenyl)azo] benzene, (Disperse Black No. 9), 4-[(4-aminophenyl)azo]-1-[di-(2-hydroxyethyl)amino]-3-methylbenzene (HC Yellow No. 7), 2,6-diamino-3-[(pyridin-3-yl)azo]-pyridine and 2-((4-(ethyl-(2-hydroxyethyl)amino)-2-methylphenyl)azo)-5-nitro-1,3-thiazole (CI111935; Disperse Blue No. 106).

Cationic basic dye useful herein includes, for example, di-[4-(diethylamino)phenyl][4-(ethylamino)naphthyl]carbenium chloride (CI42595; Basic Blue No. 7), di-[4-(dimethylamino)phenyl][4-(phenylamino)naphthyl]carbenium chloride (CI44045; Basic Blue No. 26), Basic Blue No. 77, 8-amino-2-bromo-5-hydroxy-4-imino-6-[(3-(trimethylammonio)-phenyl)amino]-1(4H)-naphthalene chloride (CI56059; Basic Blue No. 99), tri-(4-amino-3-methylphenyl) carbenium chloride (CI42520; Basic Violet No. 2), di-(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N, N,N-trimethylbenzolaminium chloride (CI112605, Basic Orange No. 69), 1-[(4-amino-2-nitrophenyl)azo]-7-(trimethylammonio)-2-naphthol chloride (Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl) azo]-7-(trimethylammonio)naphthalene chloride (CI12245; Basic Red No. 76), 3-methyl-1-phenyl-4-[(3-(trimethylammonio)phenyl)azo]pyrazol-5-one chloride (CI12719; Basic Yellow No. 57), and 1-methyl-4-((methylphenyl-hydrazono) methyl)pyridinium methyl sulfate (Basic Yellow No. 87).

Other cationic direct dyes useful herein include, for example, Benzenamine, 4-[(2,6-Dichlorophenyl)(4-Imino-3, 5-Dimethyl-2,5-Cyclohexadien-1-ylidene)Methyl]-2,6-Dimethyl-, Phosphate) (HC Blue No. 15), 1-(2-morpholiniumpropylamino)-4-hydroxy-9,10-anthraquinone methyl sulfate, and 1-[(3-(dimethylpropylaminium)propyl)amino]-4-(methylamino)-9,10-anthraquinone chloride.

Aqueous Carrier

The conditioning composition of the present invention comprises an aqueous carrier. The level and species of the carrier are selected according to the compatibility with other components, and other desired characteristic of the product. Generally, the compositions of the present invention comprise from about 20% to about 99%, preferably from about 30% to about 95%, and more preferably from about 80% to about 95% water.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product.

Gel Matrix

Preferably, the above cationic surfactants, together with high melting point fatty compounds and an aqueous carrier, form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Silicone Compound

Preferably, the compositions of the present invention contain a silicone compound. It is believed that the silicone compound can provide smoothness and softness on dry hair. The silicone compounds herein can be used at levels by weight of the composition of preferably from about 0.1% to about 20%, more preferably from about 0.15% to about 10%, still more preferably from about 0.2% to about 8%.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferably, the silicone compounds have an average particle size of from about 1 microns to about 50 microns, in the composition.

Preferably, silicone compounds useful herein include amino substituted materials. Preferred aminosilicones include, for example, those which conform to the general formula (III):

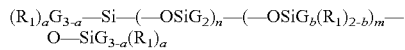

wherein G is hydrogen, phenyl, hydroxy, or $C_1$-$C_8$ alkyl, preferably methyl; a is an integer having a value from 1 to 3, preferably 1; b is 0, 1 or 2, preferably 1; n is a number from 1 to 2,000, preferably from 100 to 2,000, more preferably from 300 to 1,800; m is an integer from 0 to 1,999, preferably 0 to 10, more preferably 0; $R_1$ is a monovalent radical conforming to the general formula $C_qH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; A$^-$ is a halide ion.

One highly preferred amino silicones are those corresponding to formula (III) wherein m=0, a=1, q=3, G=methyl, n is preferably from about 1500 to about 1700, more preferably 1600; and L is —N(CH$_3$)$_2$ or —NH$_2$, more preferably —NH$_2$. Another highly preferred amino silicones are those corresponding to formula (III) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group. It is believed that, such terminal aminosilicone can provide balanced benefit between conditioning benefits and clean feel, compared to other silicones such as graft aminosilicones and silicones having no amino substitution.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

The other silicone compounds useful herein include polyalkyl or polyaryl siloxanes with the following structure:

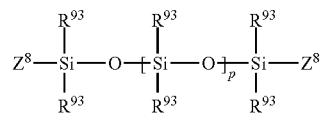

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The other silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

The silicone compounds may further be incorporated in the present composition in the form of an emulsion, wherein the emulsion is made by mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: cationic conditioning polymers including, for example, cationic celluloses such as polyquatemium-10, and cationic guar gums; additional cationic surfactant including, for example, monoalkyl quaternized ammonium salts such as behenyl trimethyl ammonium chloride and dialkyl quaternized ammonium salt such as dicetyldimethyl ammonium chloride; low melting point oils having a melting point of less than 25° C. including, for example, unsaturated fatty alcohols such as oleyl alcohol and ester oils such as pentaerythritol ester oils; polyethylene glycols; other conditioning agents such as hydrolysed collagen with tradename Peptein 2000 available from Hormel, vitamin E with tradename Emix-d available from Eisai, panthenol available from Roche, panthenol ethyl ether available from Roche, hydrolysed keratin, proteins, plant extracts, and nutrients; preservatives such as benzyl alcohol, methyl paraben, propyl paraben and Phenoxyethanol; pH adjusting agents, such as citric acid, sodium citrate, succinic acid, phosphoric acid, sodium hydroxide, sodium carbonate; salts, in general, such as potassium acetate and sodium chloride; perfumes; sequestering agents, such as ethylenediamine tetra acetic acid and its salts; and ultraviolet and infrared screening and absorbing agents such as octyl salicylate, octyl methoxycinnamate, benzophenone-3 and benzophenone-4.

Product Forms

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
(i) after shampooing hair, applying to the hair an effective amount of the conditioning compositions for conditioning the hair; and
(ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

[Compositions]

| Components | Ex. 1 | Ex. 2 | Ex. 3 | Ex. 4 | Ex. 5 | Ex. 6 |
|---|---|---|---|---|---|---|
| Behenamidopropyldimethylamine | 1.5 | 2.0 | 3.0 | — | — | — |
| Arachidamidopropyldimethylamine | — | — | — | 1.5 | 2.0 | 3.0 |
| 1-glutamic acid | 0.5 | 0.6 | 0.7 | 0.5 | 0.6 | 0.7 |
| Polyquaternium-10 *1 | — | — | — | — | — | 0.2 |
| Cetyl alcohol | 1.5 | 2.0 | 3.0 | 1.5 | 2.0 | 3.0 |
| Stearyl alcohol | 3.5 | 4.0 | 5.0 | 3.5 | 4.0 | 5.0 |
| Aminosilicone *2 | 0.5 | — | — | 0.5 | — | — |
| Dimethicone blend *3 | — | — | 4.2 | — | — | 4.2 |
| Dimethicone/Cyclomethicone *4 | — | 4.2 | — | — | 4.2 | — |
| Basic Brown 16 | 0.008 | 0.008 | 0.008 | 0.008 | 0.008 | 0.008 |

-continued

| Components | Ex. 1 | Ex. 2 | Ex. 3 | Ex. 4 | Ex. 5 | Ex. 6 |
|---|---|---|---|---|---|---|
| HC Blue No. 15 | 0.0004 | 0.0004 | 0.0004 | 0.0004 | 0.0004 | 0.0004 |
| HC Red No 10 | 0.006 | 0.006 | 0.006 | 0.006 | 0.006 | 0.006 |
| 4-Amino-3-Nitrophenol | 0.005 | 0.005 | 0.005 | 0.005 | 0.005 | 0.005 |
| UV absorbers | 0.10 | — | — | — | — | 0.10 |
| Preservatives | 0.40 | 0.40 | 0.40 | 0.40 | 0.40 | 0.40 |
| Perfume | 0.40 | 0.40 | 0.40 | 0.40 | 0.40 | 0.40 |
| Panthenol | 0.03 | — | — | — | — | — |
| Panthenyl ethyl ether | 0.03 | — | — | — | — | — |
| Deionized Water | | | q.s. to 100% | | | |

Definitions of Components
*1 Polyquaternium-10: Polymer JR30M available from Amerchol
*2 Aminosilicone: Terminal aminosilicone which is available from GE having a viscosity 10,000 mPa·s, and having following formula (III): $(R_1)_a G_{3-a}-Si-(-OSiG_2)_n-O-SiG_{3-a}(R_1)_a$ (III) wherein G is methyl; a is an integer of 1; n is a number from about 400 to about 600; $R_1$ is a monovalent radical conforming to the general formula $CqH_{2q}L$, wherein q is an integer of 3 and L is $-NH_2$
*3 Dimethicone blend: a blend of dimethicone having a viscosity of 18,000,000 mPa·s and dimethicone having a viscosity of 200 mPa·s available from GE Toshiba
*4 Dimethicone/Cyclomethicone: a blend dimethicone having a viscosity of 18,000,000 mPa·s and cyclopentasiloxane available from GE Toshiba Method of Preparation The conditioning compositions of "Ex. 1" through "Ex. 6" as shown above can be prepared by any conventional method well known in the art. They are suitably made as follows:

Cationic surfactants, high melting point fatty compounds and direct dyes are added to water with agitation, and heated to about 80° C. The mixture is cooled down to about 55° C. If included, silicone compounds, perfumes, preservatives are added to the mixture with agitation. Then the mixture is cooled down to room temperature.

Examples 1 through 6 are hair conditioning compositions of the present invention which are particularly useful for rinse-off use. The embodiments disclosed and represented by the previous "Ex. 1" through "Ex. 6" have many advantages. For example, they provide color enhancing and/or preventing color fade of colored hair. They are especially suitable for brown or brunette colored hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition comprising by weight:
   (a) from about 0.2% to about 10% of a cationic surfactant which is a salt of: (i) a tertiary amidoamine having the following general formula:

$R^1CONH(CH_2)mN(R^2)_2$ wherein $R^1$ is a straight or branched alkyl or alkenyl group of from about 20 to about 24 carbon atoms; m is an integer from 1 to 4; and $R^2$ is a $C_1$ to $C_4$ alkyl, alkenyl, alkoxyl, hydroxyalkyl, or polyoxyalkylene; and (ii) acids selected from the group consisting of 1-glutamic acid, lactic acid, hydrochloric acid, malic acid, succinic acid, acetic acid, fumaric acid, tartaric acid, and mixtures thereof;
   (b) from about 1% to about 15% of a high melting point fatty compound;
   (c) from about 0.00005% to about 0.5% of a direct dye; and
   (d) an aqueous carrier.

2. The hair conditioning composition of claim 1 wherein the amine and acid are included at a level such that the mole ratio of the amine to the acid is from about 1:0.3 to about 1:2.

3. The hair conditioning composition of claim 1 wherein $R^1$ is a straight alkyl group; and $R^2$ is a $C_1$ to $C_4$ alkyl.

4. The hair conditioning composition of claim 1 wherein the direct dye is selected from the group consisting of a nonionic direct dye, a cationic direct dye, and mixtures thereof.

5. The hair conditioning composition of claim 4 wherein the direct dye is a mixture of a nonionic direct dye and a cationic direct dye.

6. The hair conditioning composition of claim 5, wherein the nonionic direct dye is a nitro dye and the cationic direct dye is a basic dye.

7. The conditioning composition of claim 1 further comprising from about 0.1% to about 20% of a silicone compound.

8. The conditioning composition of claim 7 wherein the silicone compound is an aminosilicone having a formula:

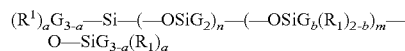

wherein G is hydrogen, phenyl, hydroxy, or $C_1$-$C_8$ alkyl; a is an integer having a value from 1 to 3; b is 0, 1 or 2; n is a number from 1 to 2,000; m is an integer from 0 to 1,999; $R_1$ is a monovalent radical conforming to the general formula $CqH_{2q}L$, wherein q is an integer having a value from 2 to 8 and L is selected from the following groups: —N(R$_2$)CH$_2$-CH$_2$—N(R$_2$)$_2$; —N(R$_2$)$_2$; —N(R$_2$)$_3$A$^-$; —N(R$_2$)CH$_2$-CH$_2$—NR$_2$H$_2$A$^-$; wherein R$_2$ is hydrogen, phenyl, benzyl, or a saturated hydrocarbon radical; A$^-$ is a halide ion.

9. The conditioning composition of claim 8 wherein the aminosilicone has a formula:

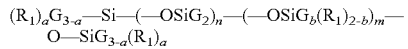

wherein G is hydrogen, phenyl, hydroxy, or C$_1$-C$_8$ alkyl; a is 1; n is a number from 100 to 2,000; m is 0; R$_1$ is a monovalent radical conforming to the general formula C$_q$H$_{2q}$L, wherein q is an integer having a value from 2 to 8 and L is —N(R$_2$)$_2$; wherein R$_2$ is hydrogen, phenyl, benzyl, or a saturated hydrocarbon radical; and A$^-$ is a halide ion.

10. The conditioning composition of claim 1 wherein the composition is substantially free of anionic surfactants and anionic polymers.

11. The conditioning composition of claim 1 which is a rinse-off hair conditioning composition.

* * * * *